(12) United States Patent
Koster et al.

(10) Patent No.: US 8,322,197 B2
(45) Date of Patent: Dec. 4, 2012

(54) METHOD AND APPARATUS FOR INJECTING A LIQUID SAMPLE IN AN HPLC ANALYZING DEVICE, AND VALVE ASSEMBLY FOR USE THEREIN

(75) Inventors: Emile Hermannus Maarten Koster, Emmen (NL); Hermannus Geert Gijlers, Emmen (NL); Rudolf Herman Robert Poot, Emmen (NL); Otto Halmingh, Odoorn (NL)

(73) Assignee: Spark Hollands B.V., Emmen (NL)

( * ) Notice: Subject to any disclaimer, the term of this patent is extended or adjusted under 35 U.S.C. 154(b) by 499 days.

(21) Appl. No.: 12/588,840

(22) Filed: Oct. 29, 2009

(65) Prior Publication Data

US 2010/0147086 A1   Jun. 17, 2010

(30) Foreign Application Priority Data

Dec. 11, 2008 (EP) .................................... 08171387

(51) Int. Cl.
*G01N 30/22* (2006.01)
*G01N 30/20* (2006.01)
(52) U.S. Cl. ..................................... 73/61.55; 73/61.56
(58) Field of Classification Search ........ 73/61.55–61.56, 73/863.72–863.73, 864.83, 864.84; 137/625.15–625.16
See application file for complete search history.

(56) References Cited

U.S. PATENT DOCUMENTS

| | | | | |
|---|---|---|---|---|
| 2,571,000 A | * | 10/1951 | Albertson | 210/135 |
| 2,979,079 A | * | 4/1961 | Turak | 137/599.03 |
| 3,080,887 A | * | 3/1963 | Brandenberg | 137/596.14 |
| 3,514,210 A | * | 5/1970 | Hrdina | 356/246 |
| 3,975,946 A | | 8/1976 | Ball et al. | |
| 4,059,009 A | * | 11/1977 | Ball et al. | 73/864.83 |
| 4,243,071 A | | 1/1981 | Shackelford | |
| 4,444,066 A | | 4/1984 | Ogle et al. | |
| 4,506,558 A | | 3/1985 | Bakalyar | |
| 4,625,569 A | * | 12/1986 | Toei et al. | 73/863.72 |
| 5,194,226 A | | 3/1993 | Tomoff et al. | |
| 5,294,052 A | * | 3/1994 | Kukesh | 239/112 |
| 6,012,487 A | | 1/2000 | Hauck | |

(Continued)

FOREIGN PATENT DOCUMENTS

EP    0 423 517 A1    4/1991

(Continued)

OTHER PUBLICATIONS from http://www.allwords.com/word-upto.html Definition of upto, AllWords.com publication, 1 page, downloaded Mar. 27, 2012.*

(Continued)

*Primary Examiner* — Thomas P Noland
(74) *Attorney, Agent, or Firm* — Oliff & Berridge, PLC (57) ABSTRACT

Method for injecting a liquid sample in an HPLC analyzing device, using an apparatus which comprises a first liquid circuit, a second liquid circuit, a valve assembly of the stator/rotor type, and a sample loop. In a first and a second valve position, respectively, the sample loop is either part of the first or of the second circuit, respectively. During the switching of the valve assembly from the second valve position into the first valve position, the valve assembly automatically and temporarily assumes an intermediate valve position in which the sample loop is automatically decompressed via a fourth connection chamber and a third valve outlet. In that intermediate valve position the sample loop is neither part of the first circuit nor part of the second circuit.

9 Claims, 3 Drawing Sheets

U.S. PATENT DOCUMENTS

| | | |
|---|---|---|
| 6,290,909 B1 | 9/2001 | Paul et al. |
| 6,382,035 B1 | 5/2002 | Nichols |
| 6,874,354 B2 | 4/2005 | Cueni et al. |
| 7,861,576 B2 * | 1/2011 | Joung ........................ 73/61.56 |
| 7,987,701 B2 * | 8/2011 | Emmert et al. ............. 73/61.56 |
| 2003/0056851 A1 * | 3/2003 | Eriksen et al. ................. 141/38 |
| 2004/0020542 A1 | 2/2004 | Cueni et al. |
| 2006/0045810 A1 | 3/2006 | Choikhet et al. |
| 2006/0249459 A1 | 11/2006 | Matabe |
| 2009/0050212 A1 | 2/2009 | Dourdeville et al. |
| 2009/0145205 A1 * | 6/2009 | Hochgraeber et al. ....... 73/61.55 |
| 2010/0058841 A1 * | 3/2010 | Wilen ........................ 73/61.56 |
| 2010/0288025 A1 * | 11/2010 | Hochgraeber ............. 73/61.55 |

FOREIGN PATENT DOCUMENTS

| | | | |
|---|---|---|---|
| EP | 440821 A1 * | 8/1991 | |
| EP | 909911 A2 * | 4/1999 | |
| WO | WO 02/39105 A1 | | 5/2002 |
| WO | WO 2006083776 A2 * | | 8/2006 |
| WO | WO 2008/005845 A2 | | 1/2008 |
| WO | WO 2010139359 A1 * | | 12/2010 |

OTHER PUBLICATIONS

Goraczko et al., "A Six-Volume Rotary Injection Valve for High Performance Liquid Chromatography," *Journal of High Resolution Chromatography Communications*, 1986, vol. 9, No. 1, pp. 61-63, in January.

Schmid, "Sample Injection in Liquid Chromatography," *Chromatographia*, 1979, vol. 12, No. 12, pp. 825-829, in December.

European Search Report issued in European Patent Application No. 08171387 on May 7, 2009, 3 pages.

* cited by examiner

METHOD AND APPARATUS FOR INJECTING A LIQUID SAMPLE IN AN HPLC ANALYZING DEVICE, AND VALVE ASSEMBLY FOR USE THEREIN

The present application is based on and claims the benefit of priority from European Patent Application No. 08171387.7 filed Dec. 11, 2008, the contents of which are incorporated wherein by reference in its entirety.

BACKGROUND

The invention relates to a method for injecting a liquid sample in an HPLC analyzing device. The invention also relates to an apparatus for injecting a liquid sample in an HPLC analyzing device. The invention furthermore relates to a valve assembly for use in such a method and in such an apparatus.

Such a method is commonly known and used in High Pressure Liquid Chromatography (HPLC), also called High Performance Liquid Chromatography. In normal HPLC, the pressure may be as high as up to around 200 bar. In case of higher pressures, up to around 1000 bar or even higher, HPLC is often more specifically referred to as Ultra High Pressure (or Performance) Liquid Chromatography (UHPLC). The invention generally relates to HPLC, and more particularly to UHPLC.

Upon completion of the said step of initializing the apparatus, the valve assembly is in the second valve position, which means that the sample loop is part of the second liquid circuit then. The second circuit, including the sample loop thereof, is containing the mobile phase then. The initial quantity of the sample has been supplied to the first liquid circuit for example by means of aspirating the sample via a needle out of a sample holder. Often, the sample holder has different compartments containing different samples. The first circuit typically is also connected to a washing liquid container and to a waste container. The liquid pressure in the first circuit is relatively low, usually equalling environmental pressure, thus giving rise to a pressure difference with the pressure of the mobile phase in the second circuit, from which second circuit there has to be injected, at a later stage, liquid with high pressure into the analyzing device.

After completion of said initializing step, the valve assembly is switched from the second valve position into the first valve position. During this switching of the valve assembly, the sample loop is losing its role as being a part of the second circuit and is attaining a role as being part of the first circuit.

In the newly attained first valve position, an additional quantity of the sample is supplied into the first circuit to such an extent that the sample loop is at least partly filled with the sample. This may for example be achieved by means of aspirating, via the needle, additional sample out of the sample holder.

By consecutively switching the valve assembly back into the second valve position, the sample in the sample loop is contained in the second circuit, so that the sample together with the mobile phase can be injected from the second circuit into the analyzing device.

A disadvantage encountered in such known methods, is explained as follows. During the abovementioned switching, directly after completion of said initializing step, of the valve assembly from the second valve position into the first valve position the high pressure mobile phase contained in the sample loop is first being cut-off from high pressure mobile phase contained in remaining sections of the second circuit. Next during the said switching, said cut-off high pressure mobile phase is being inserted into the first circuit which contains low pressure liquid. The result is that the high pressure mobile phase upon its insertion will expand in the first circuit and will therefore pass at least the first valve inlet, thus driving away the sample in the direction of the sample supply means. Thus, an uncontrolled quantity of the sample will flow out of the first circuit via the sample supply means (for example a needle).

This uncontrolled outflow is undesirable for at least the following reasons. At first, it may lead to contamination and/or cross-contamination of a sample holder. Furthermore, due to the uncontrolled outflow, the quantity of the sample between the sample supply means and the first valve inlet is not accurately known anymore. This results in problems with dosing the sample, especially in cases where the sample loop has to be only partially filled with the sample by the said supplying of the said additional quantity of the sample into the first circuit.

SUMMARY

It is an object of the invention to provide a solution according to which such unfavorable consequences of such uncontrolled outflow of sample are reliably prevented with only simple measures.

For that purpose, the invention provides a method for injecting a liquid sample in an HPLC analyzing device.

In such a method according to the invention, the intermediate valve position is automatically and temporarily attained when switching from the second valve position into the first valve position, while in that temporary intermediate valve position the cut-off high pressure mobile phase in the sample loop will expand by successively flowing through one of the first and second valve terminals, the fourth chamber and the third valve outlet. The third valve outlet may for example be in communication with the outside environment via a free ending hose connected to the third valve outlet. Thus, the mobile phase in the sample loop is automatically decompressed in the temporary intermediate valve position.

When, during the further switching of the valve assembly from the intermediate valve position into the first valve position, said cut-off and decompressed mobile phase is being inserted into the first circuit, it will not expand anymore in the first circuit and will therefore not drive away the sample in the direction of the sample supply means. Thus, a flowing out of an uncontrolled quantity of the sample via the sample supply means is reliably prevented, as well as the abovementioned unfavorable consequences thereof.

Furthermore, the measures to accomplish this result, being the provision in said first valve element and said second valve element, respectively, of such an additional third valve outlet and such an additional fourth connection chamber, respectively, are only simple measures. In fact, known methods and known apparatuses for injecting a liquid sample in an HPLC analyzing device can simply be upgraded by replacing the valve assembly of the stator/rotor type used therein by an upgraded valve assembly of the stator/rotor type having such an additional third valve outlet and such an additional fourth connection chamber. Manufacturing a valve assembly of the stator/rotor type with such an additional third valve outlet and such an additional fourth connection chamber is in principle not more complicated than manufacturing such valve assembly with the known inlets, outlets, terminals and channels.

As mentioned, the valve assembly is of the stator/rotor type and comprises a first valve element and a second valve element. The first valve element may be the stator part of the valve assembly, while the second valve element is the rotor part of the valve assembly. However, in principle it is also possible that the first valve element is the rotor part of the valve assembly, while the second valve element is the stator part of the valve assembly.

Furthermore, it is remarked that the valve assembly may comprise one or more additional inlets, outlets, terminals, connection chambers, etcetera, in its first and/or second valve elements, in addition to the mentioned first and second inlets, first, second and third outlets, first and second valve terminals, first, second, third and fourth connection chambers.

In principle, each of the mentioned valve inlets, valve outlets and valve terminals may have various shapes and may be situated at various locations of the first valve element. Furthermore, in principle, each of the mentioned connection chambers may have various shapes and may be situated at various locations of the second valve element. For example, the connection chambers may be channels, such as the circularly-arched channels known in the art for the first, second and third connection chambers. However, otherwise-arched channels, such as spirally-arched channels, or straight channels may also be applied, and even nonchannel forms are possible for the connection chambers.

In a preferable embodiment, the third valve outlet and the fourth connection chamber are arranged such that at least during the relative rotative movement about the rotation axis of the two valve elements from the second valve position into the intermediate valve position the fourth chamber continuously is in fluid communication with the third valve outlet. Such arrangements of the third valve outlet and of the fourth connection chamber stimulate a quick decompression of the sample loop in the temporary intermediate valve position.

In a further preferable embodiment of the lastmentioned preferable embodiment, the third valve outlet is arranged such that the rotation axis is enclosed by a cross section of the third valve outlet, as seen in a plane transverse to the rotation axis. This is for example the case when the rotation axis forms the center of said cross section. Thus, the third valve outlet is centrally situated within the valve assembly. Such central arrangement of the third valve outlet fits the general design requirements of HPLC valve assemblies very well and is favourable in view of compactness of the valve assembly, since the central area of the valve assembly normally is neither occupied by the first and second valve inlets, valve outlets and valve terminals, nor by the first, second and third connection chambers.

Furthermore, the invention provides an apparatus for injecting a liquid sample in an HPLC analyzing device, as well as an HPLC valve assembly of the stator/rotor.

Specific embodiments of the invention are set forth in the dependent claims.

BRIEF DESCRIPTION OF THE DRAWINGS

The invention will now be further elucidated by means of, non-limiting, examples referring to the schematic figures in the enclosed drawing, in which.

DETAILED DESCRIPTION OF THE EMBODIMENTS

Figure 1:
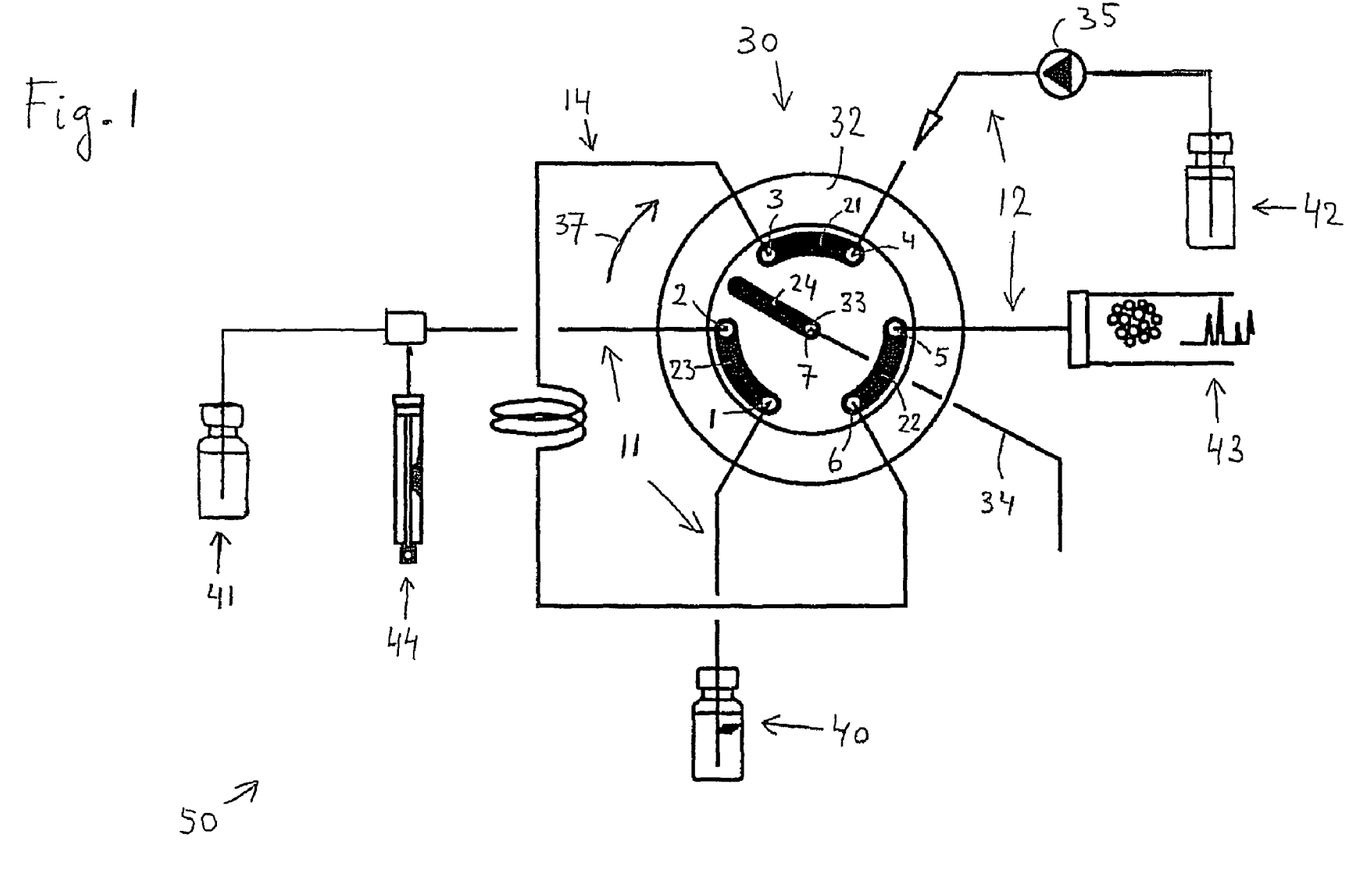
FIG. 1 shows a phase of an example of an embodiment of a method according to the invention, wherein the valve assembly is in its second valve position.
Figure 2:
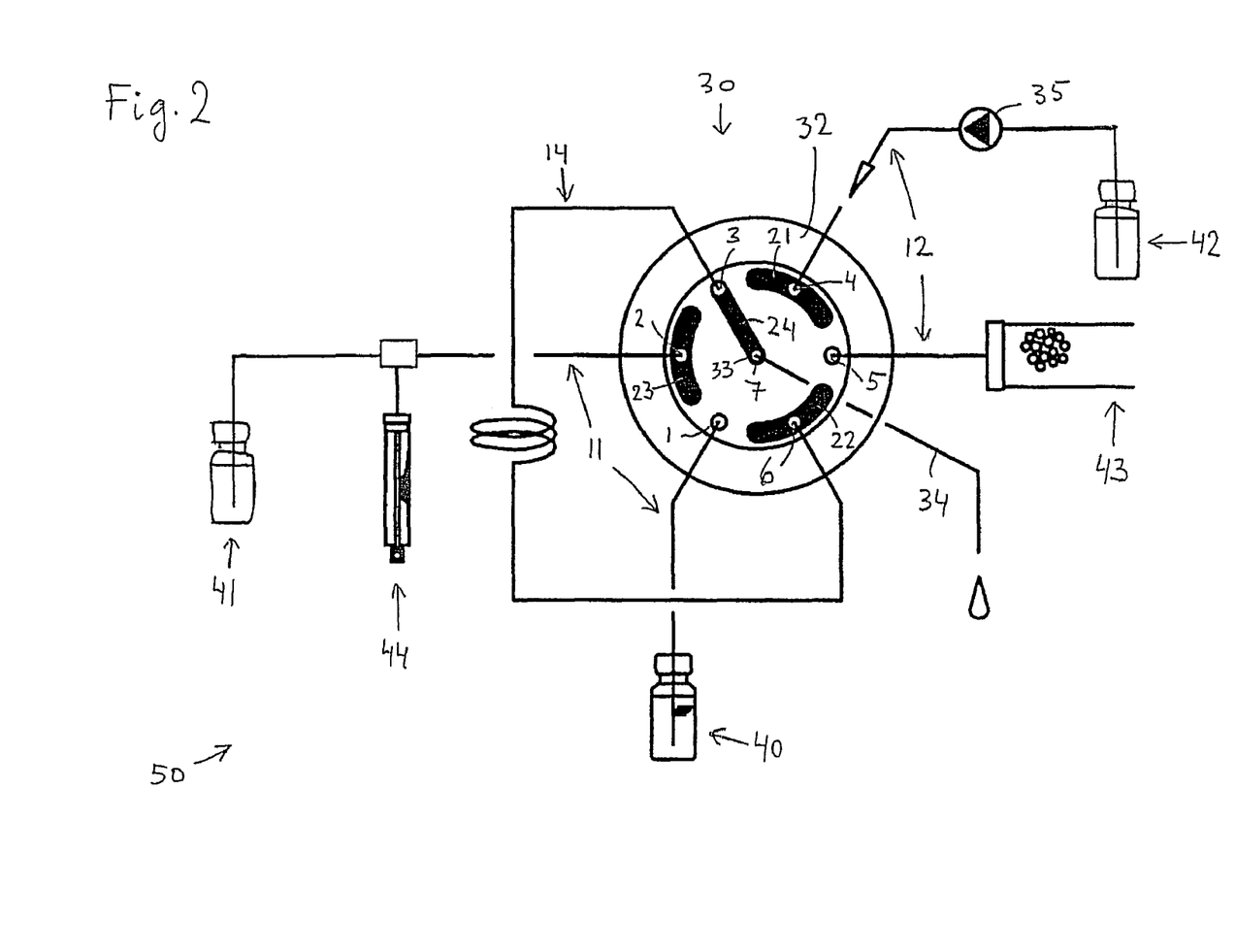
FIG. 2 shows another phase of said method embodiment, wherein the valve assembly is in its intermediate valve position.
Figure 3:
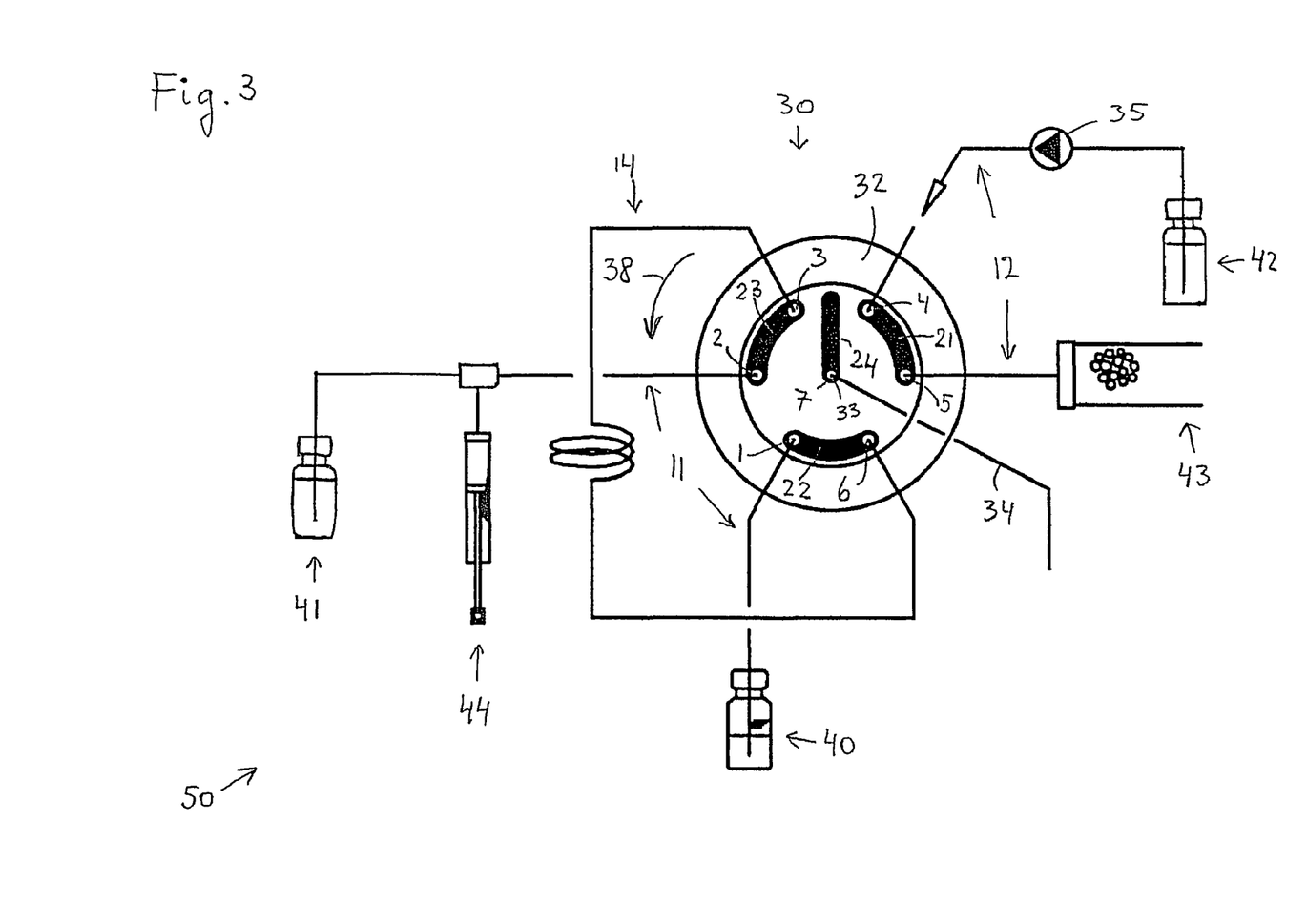
FIG. 3 shows a yet other phase of said method embodiment, wherein the valve assembly is in its first valve position.

In these figures the HPLC analysing device, for example a HPLC column, is denoted by reference numeral 43, while the apparatus for injecting a liquid sample into the analysing device 43 is denoted by reference numeral 50.

The apparatus 50 comprises a first liquid circuit 11, a second liquid circuit 12, a valve assembly 30 of the stator/rotor type, and a sample loop 14. The first circuit 11 and the second circuit 12 are connected with one another via the valve assembly 30, which comprises a first valve element and a second valve element 32 co-operating with one another and rotatable relative to one another about a rotation axis 33 for switching between different valve positions of the valve assembly. In the shown example, the first valve element is the stator of the valve assembly 30, while the second valve element 32 is the rotor of the valve assembly 30.

Both ends of the sample loop 14 are connected to the valve assembly 30 such that in a first valve position and in a second valve position of the valve assembly, respectively, the sample loop is either part of the first circuit 11 or part of the second circuit 12, respectively. The switching of the valve assembly from the second valve position (shown in FIG. 1) into the first valve position (shown in FIG. 3) is done by rotating the rotor 32 relative to the stator around the rotation axis 33 in the direction of the arrow 37, which arrow is shown in FIG. 1. The switching of the valve assembly from the first valve position (shown in FIG. 3) into the second valve position (shown in FIG. 1) is done by rotating the rotor 32 relative to the stator around the rotation axis 33 in the direction of the arrow 38, which arrow is shown in FIG. 3.

The stator comprises a first valve inlet 1 connected in the first circuit to sample supply means 40, a first valve outlet 2 connected in the first circuit to waste discharge means 41, a second valve inlet 4 connected in the second circuit to mobile phase supply means 42, a second valve outlet 5 connected in the second circuit to the analyzing device 43, a first valve terminal 3 connected to one end of the sample loop 14, and a second valve terminal 6 connected to the other end of the sample loop 14.

In the shown example, an HPLC pump 35 is included in the second fluid circuit 12. Furthermore, FIGS. 1-3 show a cylinder-piston assembly 44 included in the first liquid circuit 11. This assembly 44 is merely meant as a symbolic illustration of means for displacing liquid in the first liquid circuit 11.

The rotor 32 comprises a first connection chamber 21, a second connection chamber 22 and a third connection chamber 23. In the shown example, these connection chambers are circularly-arched channels, as known in the art, the center of the circular archs being formed by the rotation axis 33.

In the first valve position (shown in FIG. 3) the first channel 21 connects the second valve inlet 4 with the second valve outlet 5, the second channel 22 connects the second terminal 6 with the first valve inlet 1, and the third channel 23 connects the first valve outlet 2 with the first valve terminal 3. Hence, in the first valve position of FIG. 3 the sample loop 14 is part of the first circuit 11, not of the second circuit 12. Thus, when in the first valve position of FIG. 3 the HPLC pump 35 is in operation, the pump 35 will not be active on liquid contained in the sample loop 14.

In the second valve position (shown in FIG. 1) the first channel 21 connects the first valve terminal 3 with the second valve inlet 4, the second channel 22 connects the second valve outlet 5 with the second valve terminal 6, and the third channel 23 connects the first valve inlet 1 with the first valve outlet 2. Hence, in the second valve position of FIG. 1 the sample loop 14 is part of the second circuit 12, not of the first circuit 11. Thus, when in the second valve position of FIG. 1 the HPLC pump 35 is in operation, the pump 35 will indeed be active on liquid contained in the sample loop 14.

Furthermore, the stator comprises a third valve outlet 7 and the rotor 32 comprises a fourth connection chamber 24 such that during switching of the valve assembly 30 from the second valve position (shown in FIG. 1) into the first valve position (shown in FIG. 3) the valve assembly temporarily assumes the intermediate valve position (shown in FIG. 2) inbetween the second valve position and the first valve position. In the intermediate valve position the fourth chamber 24 connects the first valve terminal 3 with the third valve outlet 7, while in that intermediate valve position the sample loop 14 is neither part of the first circuit 11 nor part of the second circuit 12.

In the shown example, the third valve outlet 7 is in communication with the outside environment via a hose 34 connected to the third valve outlet 7.

Note, that in the shown example the third valve outlet 7 and the fourth connection chamber 24 are arranged such that at least during the relative rotative movement about the rotation axis 33 of the two valve elements from the second valve position into the intermediate valve position the fourth chamber 24 continuously is in fluid communication with the third valve outlet 7. More specifically, in the shown example the third valve outlet 7 is arranged such that, as seen in a plane transverse to the rotation axis 33, the rotation axis 33 is enclosed by a cross section of the third valve outlet 7. More specifically, the rotation axis 33 forms the center of said cross section. As mentioned, the fourth connection chamber 24 may have various shapes and may be situated at various locations of the rotor 32. In the shown example, the fourth connection chamber 24 has the shape of a channel whose longitudinal direction extends radially relative to the rotation axis 33.

In the situation shown in FIG. 1, initializing steps of a method according to the invention can be performed using the apparatus 50 with its HPLC valve assembly 30. In this initializing phase of the method, an initial quantity of the sample is supplied at least into a section of the first circuit 11 between the sample supply means 40 and the first valve inlet 1, and mobile phase is supplied into the second circuit 12 which includes the sample loop 14. The liquid pressure in the second circuit 12 is higher than the liquid pressure in the first circuit 11.

After this initializing phase, the valve assembly 30 is switched from the second valve position (shown in FIG. 1) into the first valve position (shown in FIG. 3). During this switching, the valve assembly 30 temporarily assumes the intermediate valve position (shown in FIG. 2). In that temporary intermediate valve position the high pressure mobile phase in the sample loop 14 will expand and decompress by successively flowing through the first valve terminal 3, the fourth channel 24 and the third valve outlet 7. Via the hose 34, some of the mobile phase may be discarded, which is symbolically indicated by means of a depicted droplet in FIG. 2. When, during the further switching of the valve assembly 30 from the intermediate valve position into the first valve position (shown in FIG. 3), said decompressed mobile phase is being inserted into the first circuit 11, it will not expand anymore in the first circuit 11.

In the then attained situation of FIG. 3, an additional quantity of the sample is supplied into the first circuit to such an extent that the sample loop 14 is at least partly filled with the sample.

Next, the valve assembly 30 is switched from the first valve position (shown in FIG. 3) into the second valve position (shown in FIG. 1) by rotating the rotor 32 relative to the stator in the direction of arrow 38, which arrow is indicated in FIG. 3. As a result, the sample in the sample loop is contained in the second circuit 12 then.

Next, the sample together with the mobile phase is injected from the second circuit 12 into the analysing device 43.

In the foregoing specification, the invention has been described with reference to specific examples of embodiments of the invention. It will, however, be evident that various modifications and changes may be made therein without departing from the broader scope of the invention as set forth in the appended claims.

For example, it is possible to apply a differently shaped first connection chamber 21 such that during the switching of the valve assembly from the second into the first valve position, it connects the second valve inlet 4 with the second valve outlet 5 at an earlier moment than shown in the Figures, for example already at the moment when the intermediate valve position of FIG. 2 is attained. This can for example be realized by designing the circularly-arched connection channel 21, as seen in FIG. 1, with a somewhat extended length from its right hand side in FIG. 1 in the direction of the arrow 37. Such an enlarged first connection chamber may be useful when applying an HPLC pump 35 which, during switching of the valve assembly, is continuously in operation. For conventional HPLC valve assemblies, such a continuously operative pump will normally not suffer from being overloaded during the normally only very short switching times (usually only several tens of milliseconds), during which switching times the second liquid circuit is interrupted for a very short time. However, for a HPLC valve assembly as used in the present invention, it might in some cases be favourable to apply a somewhat longer switching time in order to allow more time for the decompression of the liquid in the sample loop to take place in the intermediate valve position. With such longer switching time it may be beneficial to decrease the interruption time of the second circuit 12 by applying the said enlarged first connection chamber in order to prevent pump overloading.

However, other modifications, variations and alternatives are also possible. The specifications and drawings are, accordingly, to be regarded in an illustrative rather than in a restrictive sense.

The invention claimed is:

1. Method for injecting a liquid sample in an HPLC analyzing device, using an apparatus which comprises a first liquid circuit, a second liquid circuit, a valve assembly of the stator/rotor type, and a sample loop, wherein the first circuit and the second circuit are connected with one another via the valve assembly which comprises a first valve element and a second valve element co-operating with one another and rotatable relative to one another about a rotation axis for switching between different valve positions of the valve assembly, and wherein both ends of the sample loop are connected to the valve assembly such that in a first valve position and in a second valve position of the valve assembly, respectively, the sample loop is either part of the first circuit or part of the second circuit, respectively, said first valve element comprising a first valve inlet connected in the first circuit to sample supply means, a first valve outlet connected in the first circuit to waste discharge means, a second valve inlet connected in the second circuit to mobile phase supply means, a second valve outlet connected in the second circuit to the analyzing device, a first valve terminal connected to one end of the sample loop, and a second valve terminal connected to the other end of the sample loop, said second valve element comprising a first connection chamber, a second connection chamber and a third connection chamber, wherein in the first valve position the first chamber connects the second valve inlet with the second valve outlet, the second chamber connects the second terminal with the first valve inlet, and the third chamber connects the first valve outlet with the first valve terminal, while in the second valve position the first chamber connects the first valve terminal with the second valve inlet, the second chamber connects the second valve outlet with the second valve terminal, and the third chamber connects the first valve inlet with the first valve outlet;

the method comprising the consecutive steps of:
initializing the apparatus such that the valve assembly is in the second valve position, and that in this position an initial quantity of the sample is present at least in a section of the first circuit between the sample supply means and the first valve inlet, and that a mobile phase is present in the second circuit, while the liquid pressure in the second circuit is higher than the liquid pressure in the first circuit;
switching the valve assembly from the second valve position into the first valve position;
supplying an additional quantity of the sample into the first circuit to such an extent that the sample loop is at least partly filled with the sample;
switching the valve assembly from the first valve position into the second valve position, as a result of which the sample in the sample loop is contained in the second circuit; and
injecting the sample together with the mobile phase from the second circuit into the analyzing device;
wherein said first valve element comprises a third valve outlet and said second valve element comprises a fourth connection chamber such that during switching of the valve assembly from the second valve position into the first valve position the valve assembly temporarily assumes an intermediate valve position inbetween the second and the first valve positions, in which intermediate valve position the fourth chamber connects one of the first and second valve terminals with the third valve outlet, while in that intermediate valve position the sample loop is neither part of the first circuit nor part of the second circuit.

2. Method according to claim 1, wherein the third valve outlet and the fourth connection chamber are arranged such that at least during the relative rotative movement about the rotation axis of the two valve elements from the second valve position into the intermediate valve position the fourth chamber continuously is in fluid communication with the third valve outlet.

3. Method according to claim 2, wherein the third valve outlet is arranged such that, as seen in a plane transverse to the rotation axis, the rotation axis is enclosed by a cross section of the third valve outlet, such as for example when the rotation axis forms the center of said cross section.

4. Apparatus for injecting a liquid sample in an HPLC analyzing device, comprising a first liquid circuit, a second liquid circuit, a valve assembly of the stator/rotor type, and a sample loop, wherein the first circuit and the second circuit are connectable with one another via the valve assembly which comprises a first valve element and a second valve element co-operating with one another and rotatable relative to one another about a rotation axis for switching between different valve positions of the valve assembly, and wherein both ends of the sample loop are connectable to the valve assembly such that in a first valve position and in a second valve position of the valve assembly, respectively, the sample loop when thus connected is either part of the first circuit when thus connected or part of the second circuit when thus connected, respectively, said first valve element comprising a first valve inlet connectable in the first circuit to sample supply means, a first valve outlet connectable in the first circuit to waste discharge means, a second valve inlet connectable in the second circuit to mobile phase supply means, a second valve outlet connectable in the second circuit to the analyzing device, a first valve terminal connectable to one end of the sample loop, and a second valve terminal connectable to the other end of the sample loop, said second valve element comprising a first connection chamber, a second connection chamber and a third connection chamber, wherein in the first valve position the first chamber connects the second valve inlet with the second valve outlet, the second chamber connects the second terminal with the first valve inlet, and the third chamber connects the first valve outlet with the first valve terminal, while in the second valve position the first chamber connects the first valve terminal with the second valve inlet, the second chamber connects the second valve outlet with the second valve terminal, and the third chamber connects the first valve inlet with the first valve outlet;

wherein said first valve element comprises a third valve outlet and said second valve element comprises a fourth connection chamber such that during switching of the valve assembly from the second valve position into the first valve position the valve assembly temporarily assumes an intermediate valve position inbetween the second and the first valve positions, in which intermediate valve position the fourth chamber connects one of the first and second valve terminals with the third valve outlet, while in that intermediate valve position the sample loop when thus connected is neither part of the first circuit when thus connected nor part of the second circuit when thus connected.

5. Apparatus according to claim 4, wherein the third valve outlet and the fourth connection chamber are arranged such that at least during the relative rotative movement about the rotation axis of the two valve elements from the second valve position into the intermediate valve position the fourth chamber continuously is in fluid communication with the third valve outlet.

6. Apparatus according to claim 5, wherein the third valve outlet is arranged such that, as seen in a plane transverse to the rotation axis, the rotation axis is enclosed by a cross section of the third valve outlet, such as for example when the rotation axis forms the center of said cross section.

7. HPLC valve assembly of the stator/rotor type, comprising a first valve element and a second valve element co-operating with one another and rotatable relative to one another about a rotation axis for switching between different valve positions of the valve assembly, said first valve element comprising a first valve inlet connectable in a first liquid circuit to sample supply means, a first valve outlet connectable in the first circuit to waste discharge means, a second valve inlet connectable in a second liquid circuit to mobile phase supply means, a second valve outlet connectable in the second circuit to an HPLC analyzing device, a first valve terminal connectable to one end of a sample loop, and a second valve terminal connectable to the other end of the sample loop, said second valve element comprising a first connection chamber, a second connection chamber and a third connection chamber, wherein in a first valve position of the valve assembly the first chamber connects the second valve inlet with the second valve outlet, the second chamber connects the second terminal with the first valve inlet, and the third chamber connects the first valve outlet with the first valve terminal, while in a second valve position of the valve assembly the first chamber connects the first valve terminal with the second valve inlet, the second chamber connects the second valve outlet with the second valve terminal, and the third chamber connects the first valve inlet with the first valve outlet;
  so that both ends of the sample loop are connectable to the valve assembly such that in the first valve position and in the second valve position, respectively, the sample loop when thus connected is either part of the first circuit when thus connected or part of the second circuit when thus connected, respectively;
  wherein said first valve element comprises a third valve outlet and said second valve element comprises a fourth connection chamber such that during switching of the valve assembly from the second valve position into the first valve position the valve assembly temporarily assumes an intermediate valve position inbetween the second and the first valve positions, in which intermediate valve position the fourth chamber connects one of the first and second valve terminals with the third valve outlet, while in that intermediate valve position the sample loop when thus connected is neither part of the first circuit when thus connected nor part of the second circuit when thus connected.

8. Valve assembly according to claim 7, wherein the third valve outlet and the fourth connection chamber are arranged such that at least during the relative rotative movement about the rotation axis of the two valve elements from the second valve position into the intermediate valve position the fourth chamber continuously is in fluid communication with the third valve outlet.

9. Valve assembly according to claim 8, wherein the third valve outlet is arranged such that, as seen in a plane transverse to the rotation axis, the rotation axis is enclosed by a cross section of the third valve outlet, such as for example when the rotation axis forms the center of said cross section.

* * * * *

UNITED STATES PATENT AND TRADEMARK OFFICE
CERTIFICATE OF CORRECTION

PATENT NO. : 8,322,197 B2
APPLICATION NO. : 12/588840
DATED : December 4, 2012
INVENTOR(S) : Emile Hermannus Maarten Koster et al.

Page 1 of 1

It is certified that error appears in the above-identified patent and that said Letters Patent is hereby corrected as shown below:

Title Page, Item (73) Assignee should read:

(73) Assignee: Spark Holland B.V., Emmen (NL)

Title Page, Item (30) Foreign Application Priority Data should read:

(30)   Foreign Application Priority Data

Dec. 11, 2008   (EP).....................08171387.7

Signed and Sealed this
Fifth Day of March, 2013

Teresa Stanek Rea
*Acting Director of the United States Patent and Trademark Office*